United States Patent [19]
Leupold et al.

[11] Patent Number: 5,367,104
[45] Date of Patent: Nov. 22, 1994

[54] PROCESS FOR THE PURIFICATION OF ORGANIC COMPOUNDS CONTAMINATED BY DISSOLVED METAL COMPOUNDS

[75] Inventors: Ernst I. Leupold, Neu-Anspach; Udo Dettmeier, Kelkheim; Gustav Gimpel, Frankfurt am Main; Walter Reimann, Hofheim, all of Germany

[73] Assignee: Hoechst Aktiengesellschaft, Frankfurt am Main, Germany

[21] Appl. No.: 213,923

[22] Filed: Mar. 16, 1994

[30] Foreign Application Priority Data

Mar. 18, 1993 [DE] Germany .............................. 4308569

[51] Int. Cl.⁵ ............................................ C07C 17/38
[52] U.S. Cl. ..................................... 570/211; 570/190
[58] Field of Search ................................ 570/190, 211

[56] References Cited

U.S. PATENT DOCUMENTS

| | | | |
|---|---|---|---|
| 3,351,669 | 11/1967 | Anderson et al. | 568/949 |
| 3,475,495 | 10/1969 | Platz et al. | 568/492 |
| 4,885,418 | 12/1989 | Hartung | 570/211 |

FOREIGN PATENT DOCUMENTS

| | | | |
|---|---|---|---|
| 1530321 | 5/1968 | France . | |
| 1132666 | 2/1968 | United Kingdom . | |
| 0650984 | 3/1979 | U.S.S.R. | 570/211 |

*Primary Examiner*—Werren B. Lone

[57] ABSTRACT

Process for the purification of organic compounds contaminated by dissolved metal compounds.

The present invention relates to a process for the purification of organic compounds contaminated by dissolved metal compounds, by bringing the contaminated organic compound into contact with an ion exchanger resin, the functional group of which contains both a secondary amine group and a phosphonate salt radical and/or a phosphonic acid radical.

13 Claims, No Drawings

PROCESS FOR THE PURIFICATION OF ORGANIC COMPOUNDS CONTAMINATED BY DISSOLVED METAL COMPOUNDS

The present invention relates to a process for the purification of organic compounds which are contaminated by dissolved metal compounds. The contaminating metal compounds pass into the organic compound on the one hand owing to the nature of the preparation of the organic compounds and/or on the other hand owing to a corrosive action which the organic compounds exert on the walls of piping and reactor vessels. In a series of cases, the contaminants can be traced back to the use of catalysts containing metals or metal compounds. Without making a claim to completeness, examples of this which can be mentioned are the hydroformylation of olefins in the presence of appropriate catalysts, the catalytic hydrogenation of aldehydes, olefins and azomethines in the presence of solid hydrogenation catalysts and syntheses which are carried out with the aid of Lewis acids.

Thus, halogenated organic compounds, in particular halogenated or chlorinated aromatic compounds, frequently contain—owing to the nature of their preparation—small amounts of metal compounds, for example $FeCl_3$ which are added as catalyst in the halogenation or chlorination of the aromatic starting compounds.

Since organic compounds in a series of cases also exert a corrosive effect on the wall materials of the piping and reactor vessels used, metal compounds which originate from the wall material are also found in the organic compounds. In the further processing of organic compounds contaminated by dissolved metal compounds, the contaminants, which can lead for example to a discoloration of the end products or can cause faults in subsequent reaction steps, for example in the catalytic hydrogenation of chloronitroaromatic compounds, appear as undesirable. This applies, for example, to the use of organic compounds for the preparation of fine chemicals, paints, crop protection agents, as well as to their use for the preparation of polymers or pharmaceuticals for which particularly stringent demands are made regarding their purity.

For this reason the contaminating metal compounds must be removed as completely as possible.

Hitherto, only a few complex methods are known for the removal of such contaminants from nonaqueous systems. Thus, U.S. Pat. No. 3,351,669 describes the purification of halogenated phenols, which have an iron halide content of 0.001 to 2% by weight, by treatment with an anion exchanger resin which contains quaternary ammonium groups. In this process it must be ensured that iron is not present as $FeCl_3$ but $FeCl_4^-$. This is ensured by addition of HCl. Furthermore, a certain water content is necessary in order to enable the formation of the metal halide complexes and thus their separation.

However, the addition of HCl and water has considerable processing disadvantages as a consequence. On the one hand, both HCl and water, in combination with phenols promote corrosion processes, on the other hand the necessity results of having to remove these additives as completely as possible before further processing.

The object was therefore to develop a process for the purification of organic compounds, which firstly avoids these disadvantages, secondly can be practiced in an industrially simple manner and thirdly removes even very small amounts of metal compounds with high selectivity.

This object is achieved by a process for the purification of organic compounds contaminated by dissolved metal compounds. It features bringing the contaminated organic compound into contact with an ion exchanger resin, the functional group of which contains both a secondary amine group and a phosphonate salt radical and/or phosphonic acid radical.

The process according to the invention can be technically realized very simply by, for example, arranging the ion exchanger resin in the form of a fixed bed and passing the contaminated organic compound over the bed. This procedure is suitable particularly for a continuous process.

However, it is also possible to add the ion exchanger resin to the contaminated organic compound with mixing and then to separate the ion exchanger resin and organic compound from each other by sedimentation. This practice is recommended for a discontinuous procedure.

To carry out the process, both the addition of HCl and an addition of water can be dispensed with. Thus, subsequently separating off these added substances is also omitted. The contaminated organic compounds contain water either in very low quantities in accordance with its solubility or not at all. It is a particular advantage that the process can be carried out in the absence of water.

A further advantage of the process is that even small amounts of metal compound, for example $\leq 100$, in particular $\leq 50$ ppm are separated off from the organic compound not only with high selectivity but also to a very great extent. Even amounts of $\leq 10$ ppm of metal compound can still be removed by the process according to the invention in the desired extent ($\geq 90\%$).

The organic compound contains as contaminant an iron, nickel, chromium, vanadium, cobalt, copper, zinc and/or lead salt, in particular an iron, nickel, chromium and/or cobalt salt, preferably an iron, nickel and/or chromium salt in dissolved form.

The process is suitable for the purification of any type of organic compounds which are present in the liquid state under the process conditions. Examples of suitable organic compounds are aliphatic hydrocarbons, olefins, aldehydes, amines, alcohols, chlorinated aliphatic and aromatic hydrocarbons or mixtures thereof. Halogenated organic compounds can be used in the process with great success. The process is suitable particularly for the purification of halogenated aromatic compounds, in particular chlorinated or brominated aromatic compounds. Suitable halogenated aromatic compounds are, for example, unsubstituted or substituted, chlorinated nitrobenzenes, in particular ortho-, meta- and para-chloronitrobenzene, preferably meta-chloronitrobenzene.

The ion exchanger resin used must have inert behavior under the process conditions present, i.e. it must not react with the substrate to be purified. For many cases, an ion exchanger resin based on divinylbenzene-crosslinked polystyrene is suitable. However, other conventional resins, for example polyacrylates, polyacrylic acid, polyacrylamides, phenol-formaldehyde resins or polyalkylamine resins can also be used.

While carrying out the process it is recommended to use an ion exchanger resin the functional group of which corresponds to the formula $-(CH_2)_m NH(CH_2)_n PO_3 X_2$, in which m and n, independently of each other, are respectively an integer from 1 to 8, in particular 1 to 4, and X is a hydrogen atom or a metal atom, in particular an alkali metal atom.

An ion exchanger resin the functional group of which corresponds to the formula —$CH_2NHCH_2PO_3Na_2$, is particularly highly suitable.

The process according to the invention can be carried out in a relatively broad temperature range, for example from 0 to 100, in particular 20° to 80° C. Generally, the process conditions (pressure, and temperature) are selected in such a way that the organic compound is present in the liquid state or, possibly, in the dissolved state.

The process does not require any particular technical expense. No particular demands are made on the equipment which suggests itself for carrying out the purification. The process can be carried out in all equipment which is suitable for carrying out reactions in the liquid state, for example—as already mentioned above—continuously in an optionally heatable flow tube filled with the ion exchanger resin or discontinuously in a stirred vessel in which the ion exchanger resin and the organic compound to be purified are mixed to form a suspension.

The following examples confirm the invention without restricting it.

EXAMPLE 1

A commercial ion exchanger resin is used, the matrix of which is composed of polystyrene crosslinked with divinylbenzene and has a macroporous structure. The resin contains as functional group the structural element —$CH_2NHCH_2PO_3Na_2$.

30 ml of ion exchanger resin, after washing with methanol and vacuum drying, are packed into a vertically arranged heatable tube (internal diameter: 1.2 cm; length: 35 cm) which is provided at the bottom end with a stopcock. First of all the tube is filled with meta-chloloronitrobenzene which contains 10 ppm of iron in the form of $FeCl_3$. A dropping funnel filled with the same product is mounted on the top part of the tube. Tube and dropping funnel are held at 60° C. by jacket heating. By opening the stopcock, the eluate is taken off at a rate of 60 ml/h (LHSV: 2 $h^{-1}$):

| Fe concentration in the eluate | |
|---|---|
| Running time (hours) | ppm Fe |
| 10 | <1 |
| 25 | <1 |
| 50 | <1 |
| 75 | <1 |
| 100 | <1 |

Even after well over 100 hours, a virtually iron-free eluate is obtained.

EXAMPLE 2

In a heatable stirred vessel, 1 kg of m-chloronitrobenzene (Fe content: 6 ppm; Fe as $FeCl_3$) is intensively stirred at 50° C. with 1.5 g of the resin described in Example 1. Hourly samples are taken and analyzed:

| Fe concentration in the product: | |
|---|---|
| Running time (hours) | ppm Fe |
| 1 | 3.3 |
| 2 | <1 |

Comparative Example

The procedure as described in Example 2 (Fe content: 6 ppm; Fe as $FeCl_3$) is followed, but different ion exchanger resins are used. The results can be taken from the following summary:

| No. | Functional group | ppm of Fe after 5 hours of reaction time |
|---|---|---|
| A | As in Examples 1 and 2 | <1 |
| B | —NHR | 3.5 |
| C | —$NR_3$ + $Cl^-$ (according to U.S. Pat. No. 3,351,669) | 2.8 |
| D | —$SO_3H$ | 5.3 |
| E | —$CH_2$—$NH_2$ | 4.9 |

As follows from the comparative Examples B to E, separating off the $FeCl_3$ proceeds only very incompletely.

We claim:

1. A process for the purification of organic compounds contaminated by dissolved metal compounds which comprises bringing a thus—contaminated organic compound into contact with an ion exchange resin, the functional group of which contains both a secondary amine group and a phosphonate salt radical or phosphonic acid radical or a combination of a phosphonate salt radical and a phosphonic acid radical.

2. The process as claimed in claim 1, wherein a said contaminated organic compound contains a dissolved iron, nickel, chromium, cobalt, copper or lead salt or a combination of said salts.

3. The process as claimed in claim 1, wherein a said contaminated organic compound is a halogenated organic compound.

4. The process as claimed in claim 1, wherein a said contaminated organic compound is a halogenated aromatic compound.

5. The process as claimed in claim 1, wherein a said contaminated organic compound is an unsubstituted or substituted chlorinated nitrobenzene.

6. The process as claimed in claim 1, wherein said ion exchange resin comprises divinylbenzene-crosslinked polystyrene.

7. The process as claimed in claim 1, wherein the functional group of the ion exchange resin corresponds to the formula —$(CH_2)_mNH(CH_2)_nPO_3X_2$, in which m and n, independently of each other are respectively a number from 1 to 8, and X is a hydrogen atom or a metal atom.

8. The process as claimed in claim 7, wherein the functional group corresponds to the formula —$CH_2NHCH_2PO_3Na_2$.

9. The process as claimed in claim 1, wherein a said contaminated organic compound is brought into contact with the ion exchange resin at 0° to 100° C.

10. The process as claimed in claim 1, wherein a said contaminated organic is m-chloronitrobenzene.

11. The process as claimed in claim 7, wherein, in said formula, m and n, independently of each other, are numbers from 1 to 4, and X is a metal atom.

12. The process as claimed in claim 11, wherein said metal atom is an alkali metal atom.

13. The process as claimed in claim 9, wherein a said contaminated organic compound is brought into contact with the ion exchange resin at 20° to 80° C.

* * * * *